(12) United States Patent
Antonelli et al.

(10) Patent No.: US 12,256,903 B2
(45) Date of Patent: Mar. 25, 2025

(54) CALIBRATED PNEUMATIC OTOSCOPE

(71) Applicant: University of Florida Research Foundation, Inc., Gainesville, FL (US)

(72) Inventors: Patrick Joseph Antonelli, Gainesville, FL (US); William Reschly, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 398 days.

(21) Appl. No.: 17/629,987

(22) PCT Filed: Jul. 24, 2020

(86) PCT No.: PCT/US2020/043362
§ 371 (c)(1),
(2) Date: Jan. 25, 2022

(87) PCT Pub. No.: WO2021/021587
PCT Pub. Date: Feb. 4, 2021

(65) Prior Publication Data
US 2022/0257107 A1    Aug. 18, 2022

Related U.S. Application Data

(60) Provisional application No. 62/878,968, filed on Jul. 26, 2019.

(51) Int. Cl.
*A61B 1/227* (2006.01)
*A61B 1/00* (2006.01)
*A61B 1/015* (2006.01)

(52) U.S. Cl.
CPC .......... *A61B 1/227* (2013.01); *A61B 1/00055* (2013.01); *A61B 1/00057* (2013.01); *A61B 1/00068* (2013.01); *A61B 1/015* (2013.01)

(58) Field of Classification Search
CPC .............................. A61B 1/227; A61B 1/2275
See application file for complete search history.

(56) References Cited

U.S. PATENT DOCUMENTS 3,596,653 A * 8/1971 Hotchkiss ............ A61B 1/2275
359/602
3,698,387 A * 10/1972 Moore ................. A61B 1/2275
385/115

(Continued)

FOREIGN PATENT DOCUMENTS

CA          2994244 C  *  3/2022  .......... A61B 1/0661
WO  WO-2009157825 A1 * 12/2009  .......... A61B 1/00009

OTHER PUBLICATIONS

International Search Report and Written Opinion for PCT/US2020/043362 mailed on Jul. 24, 2020.

*Primary Examiner* — Julianna N Harvey
*Assistant Examiner* — Anna V. Little
(74) *Attorney, Agent, or Firm* — Thomas|Horstemeyer, LLP (57) ABSTRACT

In some embodiments according to the present disclosure, calibrated pneumatic otoscopes and retrofit calibration devices are described. In certain aspects of the present disclosure, methods of using calibrated pneumatic otoscopes are described. In certain aspects according to the present disclosure, kits containing pneumatic otoscopes are described. In certain aspects according to the present disclosure, retrofit calibration devices are described.

10 Claims, 8 Drawing Sheets

(56) References Cited

U.S. PATENT DOCUMENTS

| | | |
|---|---|---|
| 5,847,832 A | 12/1998 | Liskow et al. |
| 5,919,130 A | 7/1999 | Monroe et al. |
| 2002/0038076 A1* | 3/2002 | Sheehan ................ A61B 1/227 |
| | | 600/200 |
| 2007/0112279 A1* | 5/2007 | Iseberg .................. A61B 5/126 |
| | | 600/559 |
| 2007/0129632 A1 | 6/2007 | Voie et al. |
| 2012/0088976 A1* | 4/2012 | Shehadeh .......... A61B 1/00101 |
| | | 600/187 |
| 2013/0085441 A1 | 4/2013 | Aihara |
| 2015/0221236 A1 | 8/2015 | Forte et al. |
| 2016/0150949 A1* | 6/2016 | Patterson ............. A61B 5/6817 |
| | | 600/187 |
| 2016/0279321 A1* | 9/2016 | Bansal ................ A61M 3/0202 |
| 2017/0065803 A1 | 3/2017 | Birchall et al. |
| 2019/0142258 A1* | 5/2019 | Shelton ................... A61B 1/32 |
| | | 600/200 |
| 2019/0365292 A1* | 12/2019 | Moehring ............ A61B 5/7246 |

\* cited by examiner

CALIBRATED PNEUMATIC OTOSCOPE

CROSS-REFERENCE TO RELATED APPLICATION

This application is the 35 U.S.C. § 371 national stage entry of PCT Application No. PCT/US2020/043362, filed Jul. 24, 2020, where the PCT claims priority to, and the benefit of, U.S. Provisional Application entitled "CALIBRATED PNEUMATIC OTOSCOPE," having Ser. No. 62/878,968, filed Jul. 26, 2019, both of which are incorporated herein by reference in their entireties.

BACKGROUND

Pneumatic otoscopy is the standard of care in the diagnosis of otitis media, the most common bacterial infection of childhood. Conventional pneumatic otoscopy is performed by applying air pressure to a diagnostic otoscope head through a rubber bulb. Pressures generated with such a system may be either too low (e.g., to move a normal tympanic membrane) or too high (e.g., cause movement of a tympanic membrane in the presence of a middle ear with effusion, or cause pain). Inaccurate pressure compromises the diagnostic utility of pneumatic otoscopy and can lead to mis-diagnosis. Accordingly, there is a need to address the aforementioned deficiencies and inadequacies.

SUMMARY

Described herein are embodiments of calibrated pneumatic otoscopes, retrofit devices relating to calibrated pneumatic otoscopes, kits containing calibrated pneumatic otoscopes, and their methods of use.

In an embodiment according to the present disclosure, described herein is a calibrated pneumatic otoscope, comprising: a power source; a first light source operatively connected to the power source; a housing operatively connected to the first light source; an optical magnifying lens on an end of the housing; a speculum on an end of the housing opposite the optical magnifying lens; a light carrier to pass light from the first light source through an end of the speculum opposite the housing; a pressure generating device in fluid connection with the housing; and a safety valve.

In embodiments of the present disclosure, the safety valve can be operatively connected to a fluidic flow path of the pressure generating device.

In embodiments of the present disclosure, the fluidic flow path of the pressure generating device can comprise a tube connecting the pressure generating device and the housing.

In embodiments of the present disclosure, the safety valve can be operatively positioned in the fluidic flow path of the pressure generating device between the pressure generating device and the housing.

In embodiments of the present disclosure, the safety valve can be operatively connected to the housing.

In embodiments of the present disclosure, the safety valve can be positioned on the housing opposite the connection of the tube of the fluidic flow path with the housing.

In embodiments of the present disclosure, the safety valve can be a ball-spring valve.

In embodiments of the present disclosure, the safety valve can further comprise a housing.

In embodiments of the present disclosure, the safety valve can be configured to release pressure from the otoscope at a pressure greater than about 300 daPa to about 400 daPa.

In embodiments of the present disclosure, the calibrated pneumatic otoscope or retrofit calibration device can further comprise a pressure alert mechanism.

In embodiments of the present disclosure, the pressure alert mechanism can be a second light source configured to emit light from the housing to the user at a different wavelength than the first light source.

In embodiments of the present disclosure, the pressure alert mechanism is an audio generating device configured to emit an audio signal to the user.

In embodiments of the present disclosure, the pressure alert mechanism can generate a first alert at a lower effective pressure greater than about 200 daPa to about 300 daPa.

In embodiments of the present disclosure, the pressure alert mechanism can generate a second alert at an upper effective pressure greater than about 300 daPa to about 400 daPa.

In embodiments of the present disclosure, the first alert and second alert can be emitted wavelengths of light or audio that are different than each other.

In embodiments of the present disclosure, the calibrated pneumatic otoscope can further comprise a handle operatively connected to the housing, wherein the power source is integrated into the housing of the handle.

In embodiments of the present disclosure, the speculum can be a reusable or disposable speculum.

In embodiments of the present disclosure, an end of the speculum can be about 3 mm to about 6 mm in diameter.

In embodiments of the present disclosure, the optical magnifying lens can further comprise an adjustable diopter.

In embodiments of the present disclosure, the first light source, the second light source, or both can be a light-emitting diode (LED).

In embodiments of the present disclosure, the power source can be a battery or alternating current (AC) power.

In embodiments of the present disclosure, the battery can be a rechargeable lithium-ion battery.

Described herein are methods of using calibrated pneumatic otoscopes and otoscopes retrofitted with devices as described herein. In an embodiments of a method of using a calibrated pneumatic otoscope as described herein, the method can comprise: providing a calibrated pneumatic otoscope or otoscope retrofitted with a device as described herein; and measuring the mobility of the tympanic membrane of a subject in need thereof with the calibrated pneumatic otoscope in response to pressure changes.

In embodiments of methods according to the present disclosure, the subject in need thereof has concerns for disease of the eardrum and middle ear (eg, otitis media).

Described herein are kits. In an embodiment of a kit as described herein, a kit can comprise one or more calibrated pneumatic otoscopes of any one of claims 1 to 22; and one or more disposable specula.

In embodiments according to the present disclosure, a kit can further comprise an otoscope.

In embodiments according to the present disclosure, a kit can further comprise an annular tubular or conical flexible structure configured to snugly fit between the ear canal of a subject in need thereof and the outer diameter of the one or more disposable specula and further configured to provide an air-tight seal between the ear canal and calibrated pneumatic otoscope.

Described herein are retrofit calibration devices. In an embodiment, retrofit calibration devices as described herein can comprise: one or more adapters configured to fit inline in a fluidic connection between a pressure generating device and a housing of an otoscope; and an adjustable calibration alert.

In embodiments according to the present disclosure, the adjustable calibration alert can further comprise one or more LEDs configured to provide visual feedback to a user, a whistle configured to provide audio feedback to a user, and a diaphragm.

In embodiments according to the present disclosure, the adjustable calibration alert can be adjusted to a set pressure according to a subject on which the device will be used by a user.

In embodiments according to the present disclosure, the calibrated pressure can be adjusted by the user according to the subject on which the device will be used.

In embodiments according to the present disclosure, the retrofit calibration device can comprise a body configured to house the adapters, the body comprised of a pressure body and a switch body, wherein the diaphragm is in between the pressure body and switch body, the diaphragm further comprising contacts configured to complete a circuit in a the switch body in response to pressure from the pressure body applied to the diaphragm.

In embodiments according to the present disclosure, the circuit completion can activate at least one of the one or more LEDs. In embodiments according to the present disclosure, the circuit completion can activate at least one of the one or more audible (to the user) audio alerts.

In embodiments according to the present disclosure, the safety valve can be a retrofit calibration device as described herein.

In embodiments according to the present disclosure, a circuit completed in the retrofit calibration device can be configured to send a signal to activate the pressure alert mechanism.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIG. 4 is an embodiment 100 of the present disclosure. According to the embodiment of FIG. 4 the assembled body of the device 101 is inline with a standard Welch Allyn pneumatic otoscope 103. The device 101 is in fluid connection with the otoscope 103 and the pressure-generating device 105 by tubing 107a and 107b.

FIG. 5 is another view of the embodiment 100 of FIG. 4. As can be seen in the view of FIG. 5, pressure chambers 109 allow pressure generated by the pressure generating device 105 (i.e. bulb) to push on a diaphragm. A communicating port 111 is also drilled between the pressure chambers that allows flow through the pressure body as well as equalization of pressure between the chambers 109.

FIG. 6 is another view of the embodiment 100 of FIG. 4. As can be seen in the view of FIG. 6, pressure from the pressure generating device 105 is applied through the pressure chambers 109 to the diaphragm 115. The applied pressure pushes the diaphragm 115 and contacts 113 into a switch mechanism (not pictured), completing a circuit and powering a visual indicator (such as light emitting diodes, or LEDs).

FIG. 7 is another view of the interior of the body 101 of the embodiment 100. When pressure is applied through the pressure body the contacts 113 in the diaphragm are pushed into contact with the switch below. The switch plates 117 are at different heights within the switch body allowing the device to sense two different pressures.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of mechanical engineering, fluid motion, and otology.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently disclosed subject-matter.

About: The term "about", when used herein in reference to a value, refers to a value that is similar, in context to the referenced value. In general, those skilled in the art, familiar with the context, will appreciate the relevant degree of variance encompassed by "about" in that context.

Associated with: Two events or entities are "associated" with one another, as that term is used herein, if the presence, level and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Comparable: As used herein, the term "comparable" refers to two or more agents, entities, situations, sets of conditions, etc., that may not be identical to one another but that are sufficiently similar to permit comparison there between so that one skilled in the art will appreciate that conclusions can reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Composition: Those skilled in the art will appreciate that the term "composition", as used herein, can be used to refer to a discrete physical entity that comprises one or more specified components. In general, unless otherwise specified, a composition can be of any form—e.g., gas, gel, liquid, solid, etc.

Comprising: A composition or method described herein as "comprising" one or more named elements or steps is open-ended, meaning that the named elements or steps are essential to a particular aspect or embodiment, but other elements or steps can be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and can also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step can be substituted for that element or step.

"Improved," "increased" or "reduced": As used herein, these terms, or grammatically comparable comparative terms, indicate values that are relative to a baseline value or reference measurement. For example, in some embodiments, an assessed value achieved with an agent of interest may be "improved" relative to that obtained or expected in the absence of treatment or with a comparable reference agent or control. Alternatively, or additionally, in some embodiments, an assessed value achieved with an agent of interest may be "improved" relative to that obtained in the same subject or system under different conditions (e.g., prior to or after an event such as administration of an agent of interest), or in a different, comparable subject (e.g., in a comparable subject or system that differs from the subject or system of interest). In some embodiments, comparative terms refer to statistically relevant differences (e.g., that are of a prevalence and/or magnitude sufficient to achieve statistical relevance). Those skilled in the art will be aware, or will readily be able to determine, in a given context, a degree and/or prevalence of difference that is required or sufficient to achieve such statistical significance.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Subject: As used herein, the term "subject" refers to an organism, typically a mammal (e.g., a human). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a subject. In some embodiments, a subject is an individual to whom diagnosis and/or therapy is and/or has been administered.

Subject in need thereof: a subject in need thereof can be a subject as described herein for which there exists a risk, potential, or existence of an otological disease.

DISCUSSION

Described herein are devices, methods, and kits relating to calibrated pneumatic otoscopes.

Described herein are calibrated pneumatic otoscopes and retrofit calibration devices configured to retrofit onto existing otoscopes. In certain aspects, calibrated pneumatic otoscopes can comprise: a power source; a first light source operatively connected to the power source; a housing operatively connected to the first light source; an optical magnifying lens on an end of the housing; a speculum on an end of the housing opposite the optical magnifying lens; and a light carrier to pass light from the first light source through an end of the speculum opposite the housing;

The power source can be, for example, a battery (such as a lithium-ion battery) housed in the handle that can be used by the user, or can be an alternating or direct current from another source (i.e. it can be hardwired into the electrical system of the room in which it is to be used).

The light source can be, for example, a light-emitting diode. Light from the light source can be channeled through a light carrying structure (such as a fiber optic plastic) towards the end of the speculum so that light is emitted from an open end of the speculum towards a subject.

The calibration component of pneumatic otoscopes as described herein can comprise a separate component to be used with conventional, non-calibrated pneumatic otoscopes, or it can be embedded in the housing. The housing can be connected to a handle that can be held by a user. The housing can comprise an end with an optical magnifying glass through which a user can look. The housing can also comprise an end configured to be or configured to receive a speculum. The speculum can be a frustroconical structure with a wide base attached to the housing and a narrow end opposite the housing with an aperture that is configured to focus light towards the ear canal of a subject.

The optical magnifying lens is a structure though which the user looks in order to see a region of interest of a subject at the end of the speculum, for example a structure within the ear canal of the subject. The optical magnifying lens can be glass or plastic or other structure. With the magnifying lens in place, air delivered to the chamber drives air into the speculum. When necessary, the magnifying lens may be rotated off the housing to allow manipulation of the ear canal through the speculum.

Speculums as described herein can be reusable or disposable for hygienic purposes. Speculums as described herein can be sterilized, for example, by way of a standard autoclave. In certain aspects, the speculum may also be a structure that is contiguous with the housing.

Calibrated pneumatic otoscopes contain a pressure generating device. In an embodiment, the pressure generating device is a bulb made out of a composition, such as rubber, then can create a pressure by way of a tube (also referred to herein as a fluidic flow path) in the housing of the otoscope that can exit the speculum (i.e. is fluidly connected with the housing).

Calibrated pneumatic otoscopes can also contain a pressure release valve (also referred to herein as a safety valve). The pressure release valve can be on the housing of the otoscope. The pressure release valve can be in line with a fluidic flow path of a pressure generating device and the housing of the otoscope. The housing of the pressure relief valve can be a hygienic housing.

The pressure release valve can be calibrated for a pressure. In keeping with pressure ranges administered during tympanometry, the pressure threshold can be from 200 to 400 daPa. The calibrated pressure can be about 210 to about 390 daPa. The calibrated pressure can be about 220 to about 380 daPa. The calibrated pressure can be about 230 to about 370 daPa. The calibrated pressure can be about 240 to about 360 daPa. The calibrated pressure can be about 240 to about 350 daPa. The calibrated pressure can be about 250 to about 340 daPa. The calibrated pressure can be about 260 to about 330 daPa. The calibrated pressure can be about 270 to about 320 daPa. The calibrated pressure can be about 280 to about 310 daPa. The calibrated pressure can be about 290 to about 300 daPa.

The calibrated pressure can be about −401 to about +401 daPa. The calibrated pressure can be about −390 to about +390 daPa. The calibrated pressure can be about −380 to about +380 daPa. The calibrated pressure can be about −370 to about +370 daPa. The calibrated pressure can be about −360 to about +360 daPa. The calibrated pressure can be about −350 to about +350 daPa. The calibrated pressure can be about −340 to about +340 daPa. The calibrated pressure can be about −330 to about +330 daPa. The calibrated pressure can be about −320 to about +320 daPa. The calibrated pressure can be about −310 to about +310 daPa. The calibrated pressure can be about −300 to about +300 daPa. The calibrated pressure can be about −290 to about +290 daPa. The calibrated pressure can be about −280 to about +280 daPa. The calibrated pressure can be about −270 to about +270 daPa. The calibrated pressure can be about −260 to about +260 daPa. The calibrated pressure can be about −250 to about +250 daPa. The calibrated pressure can be about −240 to about +240 daPa. The calibrated pressure can be about −230 to about +230 daPa. The calibrated pressure can be about −220 to about +220 daPa. The calibrated pressure can be about −210 to about +210 daPa. The calibrated pressure can be about −200 to about +200 daPa. The calibrated pressure can be about −190 to about +190 daPa. The calibrated pressure can be about −190 to about +190 daPa. The calibrated pressure can be about −180 to about +180 daPa. The calibrated pressure can be about −170 to about +170 daPa. The calibrated pressure can be about −160 to about +160 daPa. The calibrated pressure can be about −150 to about +150 daPa. The calibrated pressure can be about −140 to about +140 daPa. The calibrated pressure can be about −130 to about +130 daPa. The calibrated pressure can be about −120 to about +120 daPa. The calibrated pressure can be about −110 to about +110 daPa. The calibrated pressure can be about −100 to about +100 daPa. The calibrated pressure can be about −90 to about +90 daPa. The calibrated pressure can be about −80 to about +80 daPa. The calibrated pressure can be about −70 to about +70 daPa. The calibrated pressure can be about −60 to about +60 daPa. The calibrated pressure can be about −50 to about +50 daPa. The calibrated pressure can be about −40 to about +40 daPa. The calibrated pressure can be about −30 to about +30 daPa. The calibrated pressure can be about −20 to about +20 daPa. The calibrated pressure can be about −10 to about +10 daPa.

The pressure release valve can be configured to be in operative communication or fluidic communication with the housing or a fluidic flow path from the pressure generating device to the house so that if a pressure greater than the calibrated pressure is generated, pressure is released from the system through an outlet in the valve, or other outlet.

In embodiments according to the present disclosure, the sensitivity of the pressure release valve can be adjusted by the user according to the needs of the subject in which the otoscope is to be used. Such sensitivity adjustment can be made mechanically on the valve, or by way of a digital circuit in communication with valve. For example, for adult patients or larger subjects, the full pressure range could be employed, whereas for smaller subjects, for example pediatric subjects, the pressure range can be adjusted to be a narrower value to fit the subject according to the needs of the user.

In an embodiment, the pressure relief valve comprises a membrane and a diaphragm configured to deform, creating an acoustic "pop" at a set pressure (for example 200 daPa) and a spring that is configured to release at a higher pressure (for example 400 daPa), and an outflow port from which pressure can be released.

Optionally calibrated pneumatic otoscopes can also contain an alert that can alert a user if the generated pressure is the calibrated pressure, lower than the calibrated pressure, or higher than the calibrated pressure.

In certain aspects the alert can be an optical alert, such as a light generated by a light source, for example an LED. The light source, for example, can emit light of a wavelength (for example green in the visible spectrum) when the pressure generated is the calibrated pressure, and can emit light of a different wavelength (for example red in the visible spectrum) if the pressure generated is higher or lower than the calibrated pressure. The light source of the alert light can be, for example, an LED inside the housing of the otoscope that can be viewed through the lens or can be otherwise positioned such that a user can see it.

In an embodiment, a LED alert can be a LED switch that comprises a flexible diaphragm mechanically connected to an electrical conductor configured to contact LED circuit contact points upon flexion of the flexible diaphragm. Upon completion of the circuit by contact of the electrical conductor with the LED contact points, a voltage or other signal can be sent to a LED which will provide a visual signal. The LED switch can receive power from the power source (battery or other power source, such as AC power), and can further comprise a chamber open to atmospheric pressure via a tunable outflow tract.

In certain aspects, the alert can be an audible alert that does not require visual inspection by the user. The alert can be a sound generated at a wavelength when the generated pressure is the calibrated pressure and can be a sound generated at a different wavelength when the generated pressure is higher or lower than the calibrated pressure. Such alert can be generated by a speaker. In an embodiment, such an alert can be a mechanical sound generation device, for example a whistle.

Additional aspects and examples of otoscopes and methods of use according to the present disclosure can be found in, for example, in "Quantitative Pneumatic Otoscopy Using a Light-Based Ranging Technique" by Shelton et al. (JARO 18:555-568 (2017)) and "Emerging Technologies for the Diagnosis of Otitis Media" by Marom al. DOI: et (Otolaryngology-Head and Neck Surgery 1-10; 10.1177/0194599818809337), both of which are incorporated herein by reference in their entireties.

Also described herein are retrofit calibration devices. Retrofit calibration devices as described herein can comprise: a main body; an adapter configured to fit in line with the fluidic connection of the pressure generating device (for example a flexible tube) and the housing in between the pressure generating device and the housing; and an adjustable/tunable calibration alert. In certain aspects, the adjustable/tunable calibration alert can comprise a device that can generate an audible signal, for example a mechanical whistle, a diaphragm, and a light source that can provide a visual alert. The alert can be adjusted/tuned to a desired sensitivity by the user according to the needs of the subject. If, for example, the subject is a large adult subject, the sensitivity of the alert can be adjusted to a full range of pressures as described herein, but if, for example, the subject is a smaller pediatric subject, the alert can be adjusted for a narrower pressure range as described herein.

Methods of Use

Also described herein are methods of using calibrated pneumatic otoscopes according to the present disclosure.

Methods as described herein can comprise providing a subject or subject in need thereof, inserting the speculum of a calibrated pneumatic otoscope as described herein into the ear canal, generating pressure in the housing of the calibrated pneumatic otoscope to a desired pressure within a desired pressure range, and taking a measurement from the subject. Methods as described herein can further comprise creating a seal between the ear canal of the subject and the speculum. Methods as described herein can further comprise determining an otitis status from the measurement of the subjects' ear canal.

Kits

Described herein are kits containing calibrated pneumatic otoscopes or parts thereof. Kits as described herein, in an embodiment, can comprise one or more calibrated pneumatic otoscopes of any one of claims 1 to 10; and one or more disposable specula. Kits as described herein can further comprise an otoscope. Kits as described herein can further comprise an annular tubular or conical flexible structure configured to snugly fit between the ear canal of a subject in need thereof and the outer diameter of the one or more disposable specula and further configured to provide an air-tight seal between the ear canal and calibrated pneumatic otoscope.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

Other features, objects, and advantages of the present invention are apparent in the description that follows. It should be understood, however, that the description, while exemplifying certain embodiments of the present invention, is given by way of illustration only, not limitation. Various changes and modifications within the scope of the invention will become apparent to those skilled in the art from the detailed description.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Figure 1A:
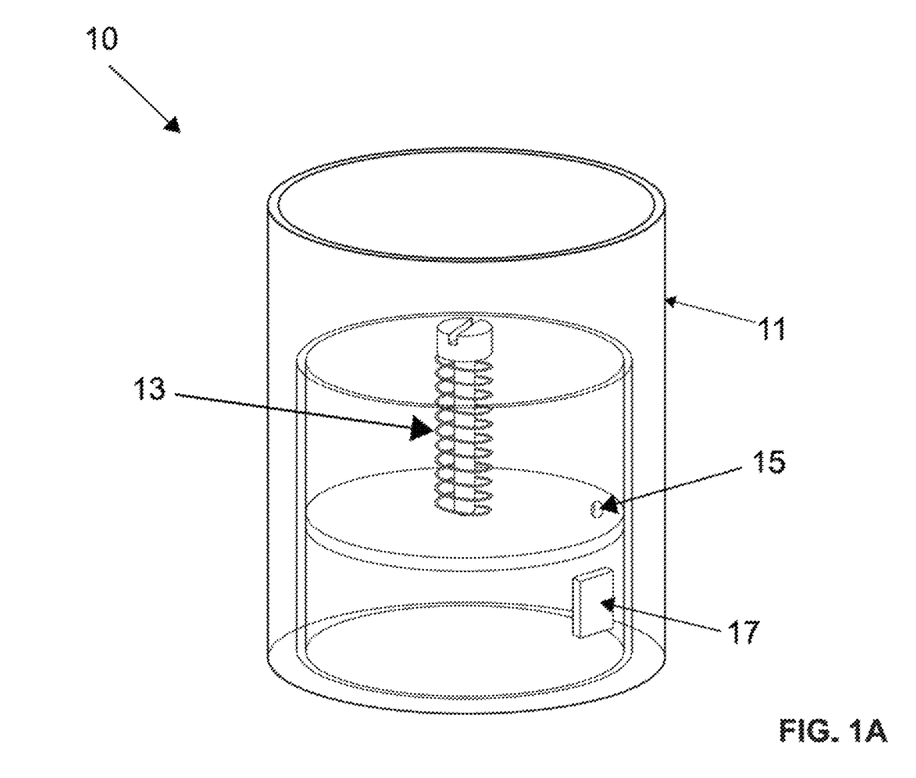
FIG. 1A is an embodiment of a pressure relief valve 10 (also referred to as a safety valve) according to the present disclosure.
Figure 1B:
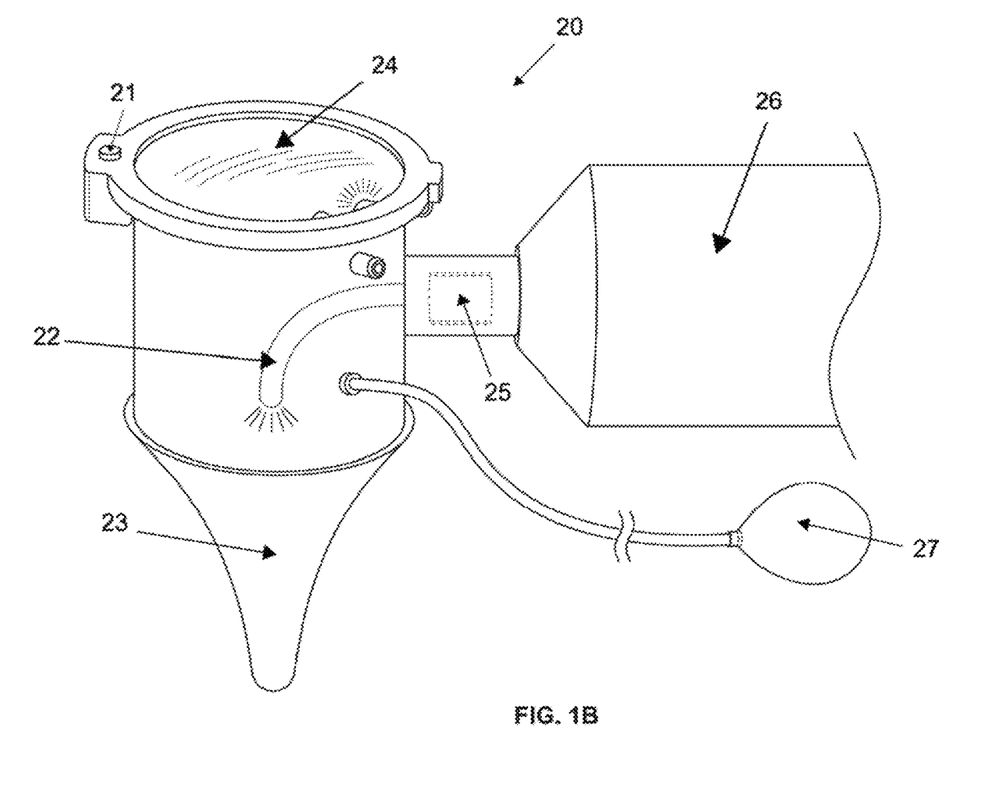
FIG. 1B is an embodiment of a calibrated pneumatic otoscope 20 as described herein.

FIG. 1A shows an embodiment of a pressure release valve 10 for a calibrated pneumatic otoscope as described herein. As can be seen in FIG. 1A, the pressure release (or safety) valve 10 includes a hygienic housing 11, a spring 13 set to release at a pressure of 400 daPa, an outflow membrane 15, and a diaphragm 17 calibrated to pop at a set pressure (e.g., 200 daPa). FIG. 1B shows an embodiment of a calibrated pneumatic otoscope 20 as described herein. As can be seen in FIG. 1B, the pneumatic otoscope 20 includes a bolt 21 and a magnifying lens 24, a light carrier 22, a LED bulb 25, a speculum 23, a battery 26, and a squeeze bulb 27.

Example 2

Figure 2:
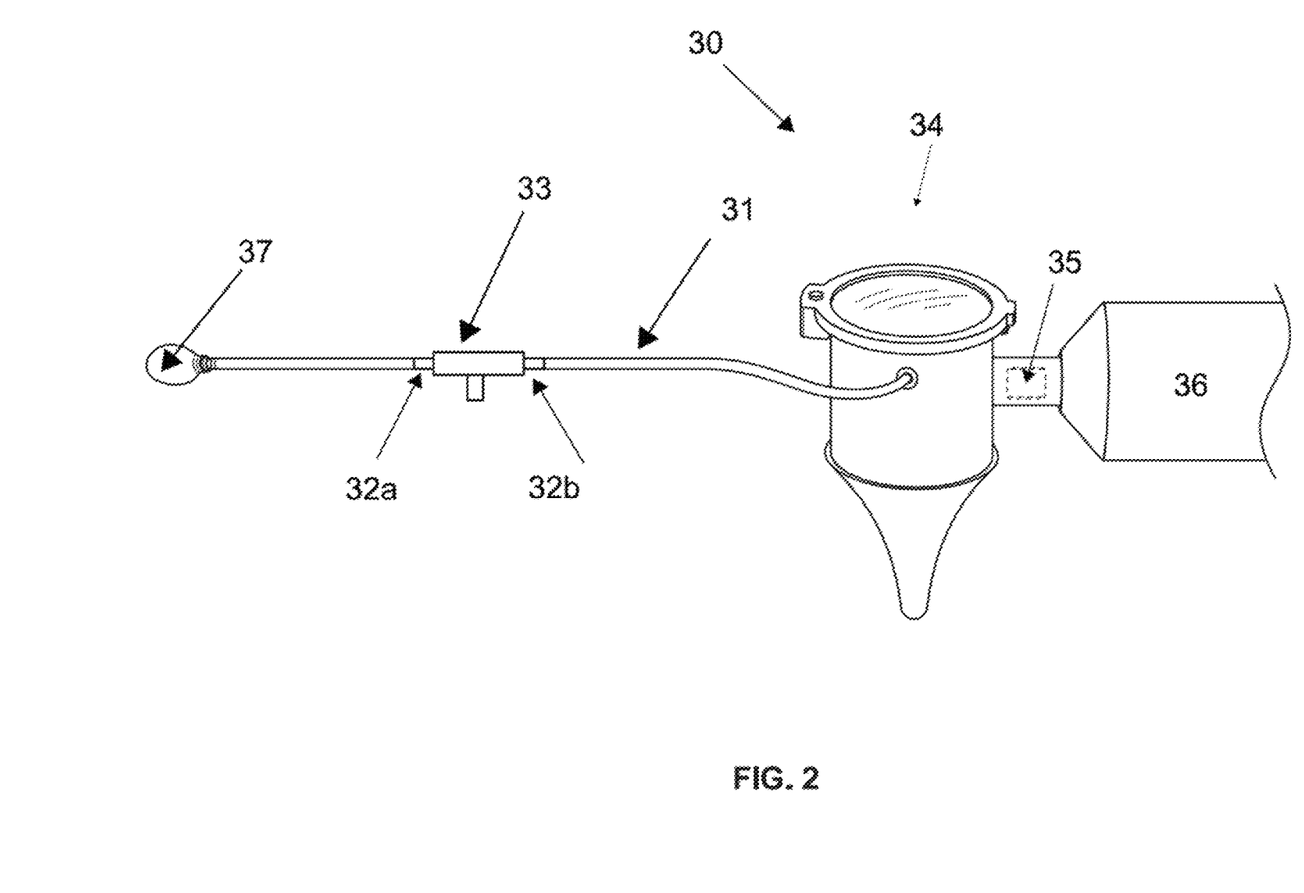
FIG. 2 is an embodiment of a pressure relief valve/calibration device 30 according to the present disclosure that is configured to be retrofitted onto existing otoscopes.

FIG. 2 shows an embodiment of a retrofit calibration device 30 according to the present disclosure. As can be seen in the embodiment 30 of FIG. 2, the retrofit calibration device can comprise a main body 33 with an adapter (32a and 32b) configured to fit in line with the fluidic connection 31 between the pressure generating device 37 and the housing of the otoscope. A battery/handle 36 can be seen, as well as an LED bulb 35 and otoscope head 34. The retrofit calibration device can further comprise a device for generating an audible signal, such as a mechanical whistle, a diaphragm, and a LED. The LED can be in electrical communication with a LED switch as described herein. The retrofit calibration device can be adjusted or tuned by the user according to the needs of the subject as described herein.

Example 3

The device can comprise a handle (which can have an integrated power source, such as a battery), a port for the pneumatic tubing-pressure generating bulb assembly, a bolt that allows the magnifying lens to rotate, and a calibration alert (which can be viewed by the user through the lens). The calibration alert can comprise a device for generating a visual alert (for example a LED), a device for generating an audible alert (a tone, for example from a mechanical whistle), and a diaphragm.

Example 4

Figure 3:
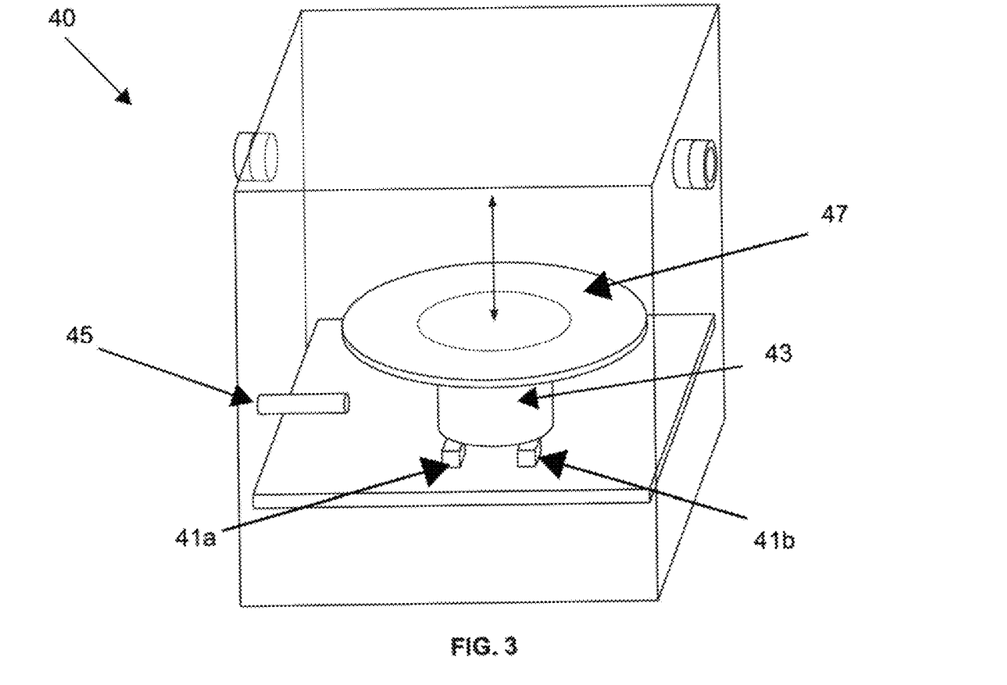
FIG. 3 is an embodiment of a light emitting diode (LED) switch 40 that is configured to provide a visual alert according to a measured pressure.

FIG. 3 is an embodiment of a LED switch 40 as described herein. As shown in FIG. 3, the embodiment of the LED switch 40 can comprise a flexible diaphragm 47 mechanically connected to an electrical conductor 43 that is configured to complete a circuit upon contact of the conductor with LED circuit contact points 41a and 41b (one from battery, another to the LED) as a result of flexion of the diaphragm 47. A voltage or other signal can then be sent to a LED to provide visual feedback to a user of the device that is in communication with the switch. The switch can receive power from the power source, for example a battery or AC power, and can further comprise a chamber that is open to atmospheric pressure via a tunable outflow tract 45.

Example 5

Pneumatic otoscopes apply pneumatic pressure to the otoscope head and external auditory canal by squeezing a rubber bulb or generating pressure by other means. However, there is currently no way to determine if adequate pressure has been applied by the operator to cause movement of the tympanic membrane of the subject. Described herein is a calibrated pressure sensing device that is in line with a pneumatic otoscope with visual feedback to let the operator know when set minimum and maximum pressures have been reached.

Figure 4:
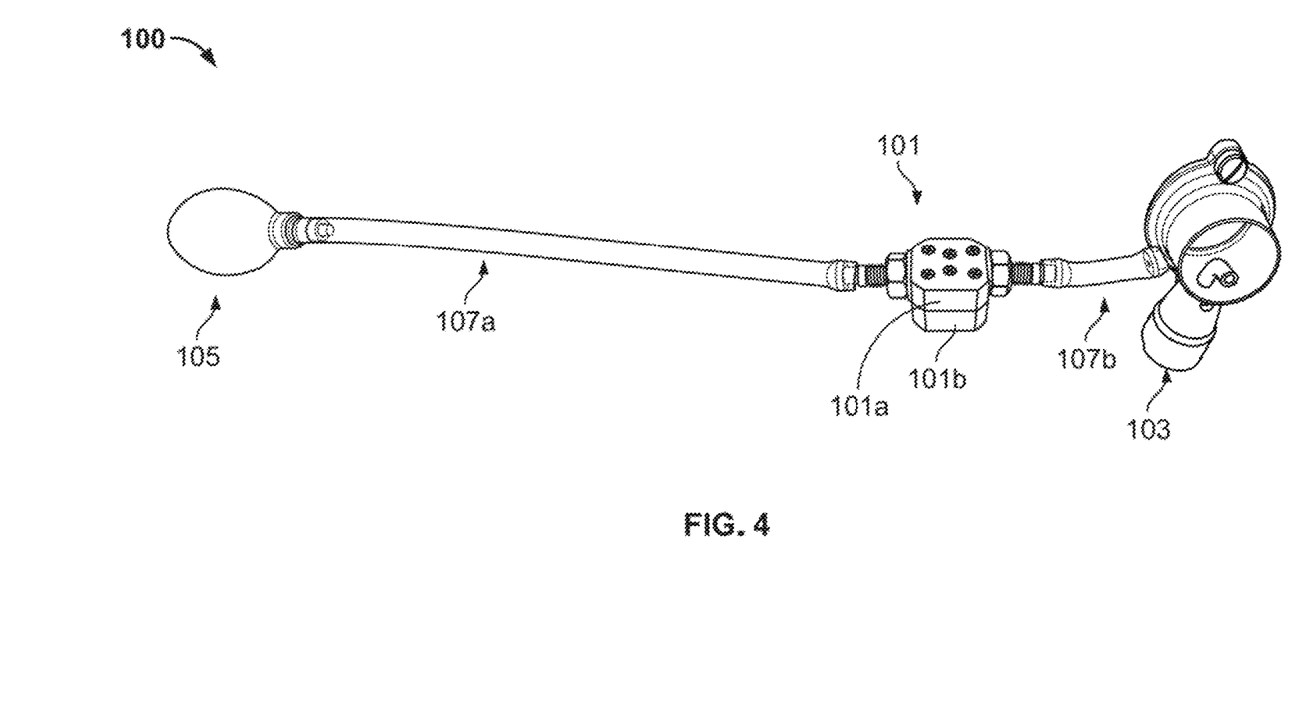

FIG. 4 is a photograph showing an embodiment 100 of the present disclosure. According to the embodiment of FIG. 4, the assembled body of the device 101 is in line with a standard Welch Allyn pneumatic otoscope 103. The device 101 is in fluid connection with the otoscope 103 and the pressure-generating device 105 by tubing 107a and 107b.

The body of the device 101 can be comprised of two pieces and can split into two halves—the pressure body 101a and the switch body 101b. The body of the device 101 comprises a pressure body 101a and a switch body 101b that sandwich electrical contacts 113 and a diaphragm 115 (pictured in FIG. 6 below).

Figure 5:
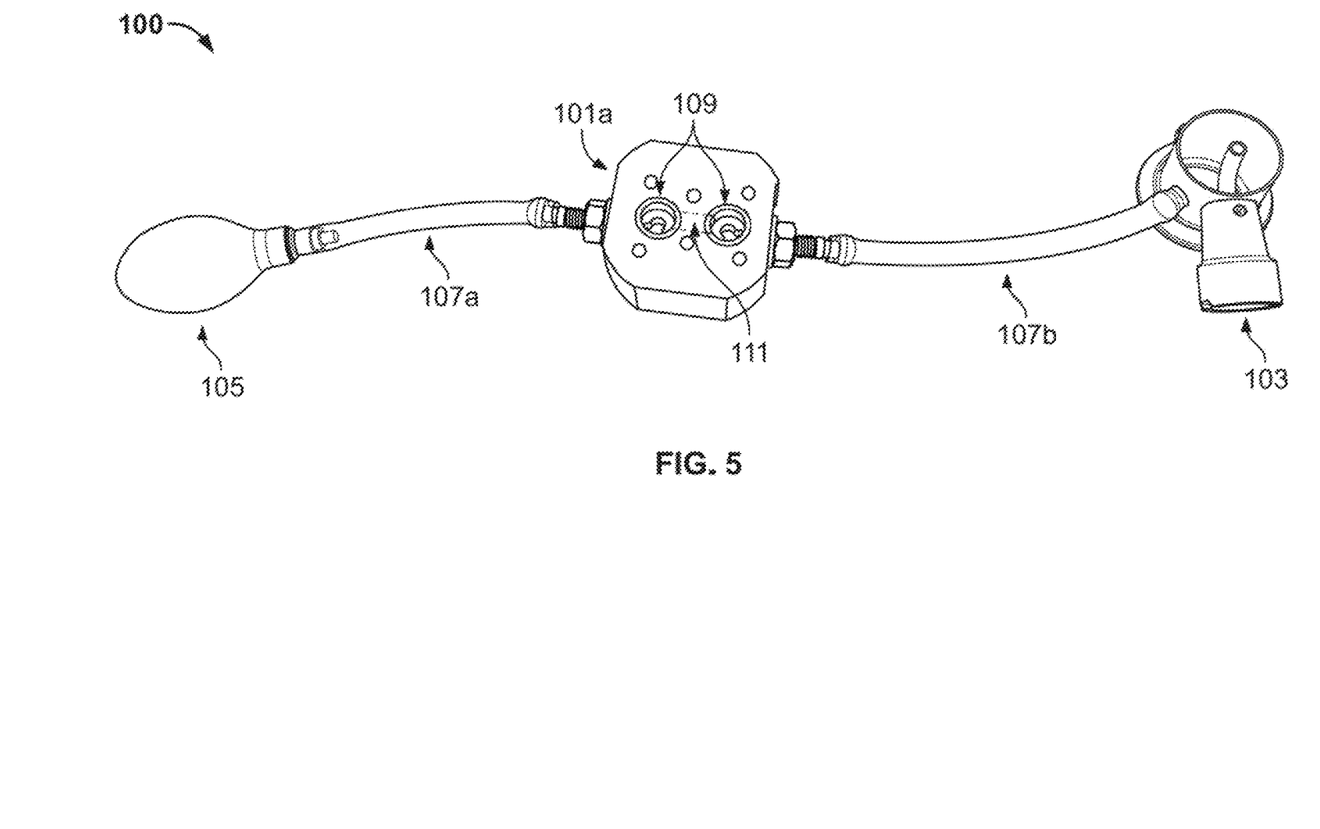

FIG. 5 is another view of the embodiment 100 of FIG. 4 showing the device 101 disassembled, revealing the interior of the pressure body 101a. FIG. 5 shows the interior side of the pressure body 101a that faces the switch body 101b and is in communication with the bulb 105 and otoscope head 103. As can be seen in the view of FIG. 5, pressure chambers 109 allow pressure generated by the pressure generating device 105 (i.e. bulb) to push on a diaphragm. A communicating port 111 is also drilled between the pressure chambers that allows flow through the pressure body as well as equalization of pressure between the chambers 109.

Figure 6:
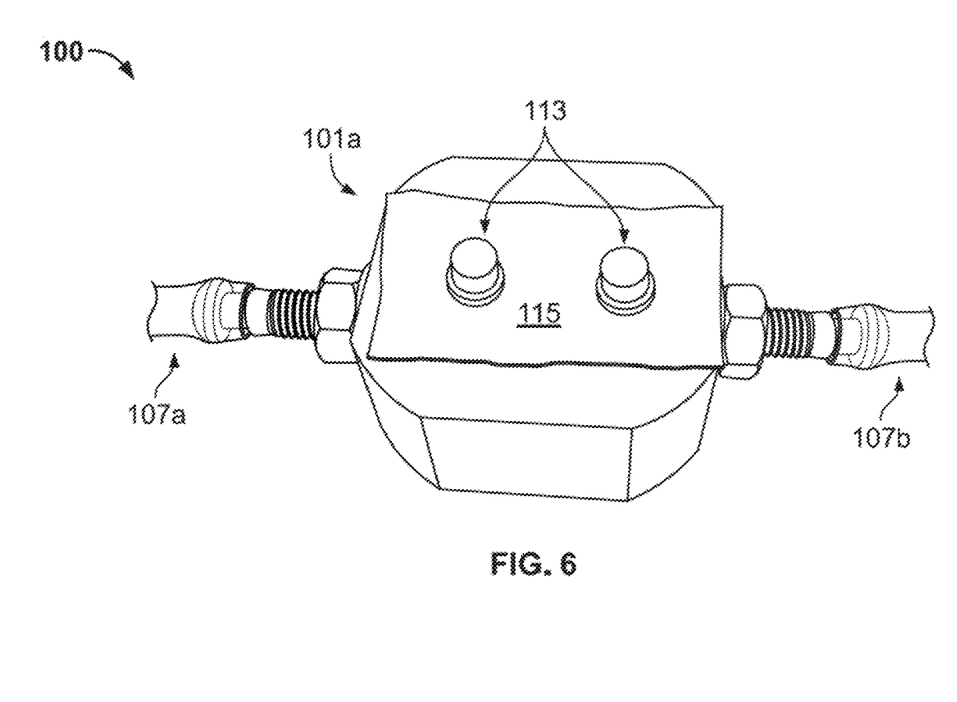

FIG. 6 is another view of the embodiment 100 of FIG. 4. Pressure via the pressure chambers 109 is applied to the diaphragm 115. The pressure pushes the diaphragm 115 and contacts 113 into the switch mechanism of the switch body 101b, competing a circuit and powering light emitting diodes (LED).

As can be seen in the view of FIG. 6, pressure from the pressure generating device 105 is applied through the pressure chambers 109 of the pressure body 101a to the diaphragm 115. The applied pressure pushes the diaphragm 115 and contacts 113 into a switch mechanism (not pictured), completing a circuit and powering a visual indicator (such as light emitting diodes, or LEDs). The contacts and diaphragm are "sandwiched" in the middle of the pressure body 101a and switch body 101b.

Figure 7:
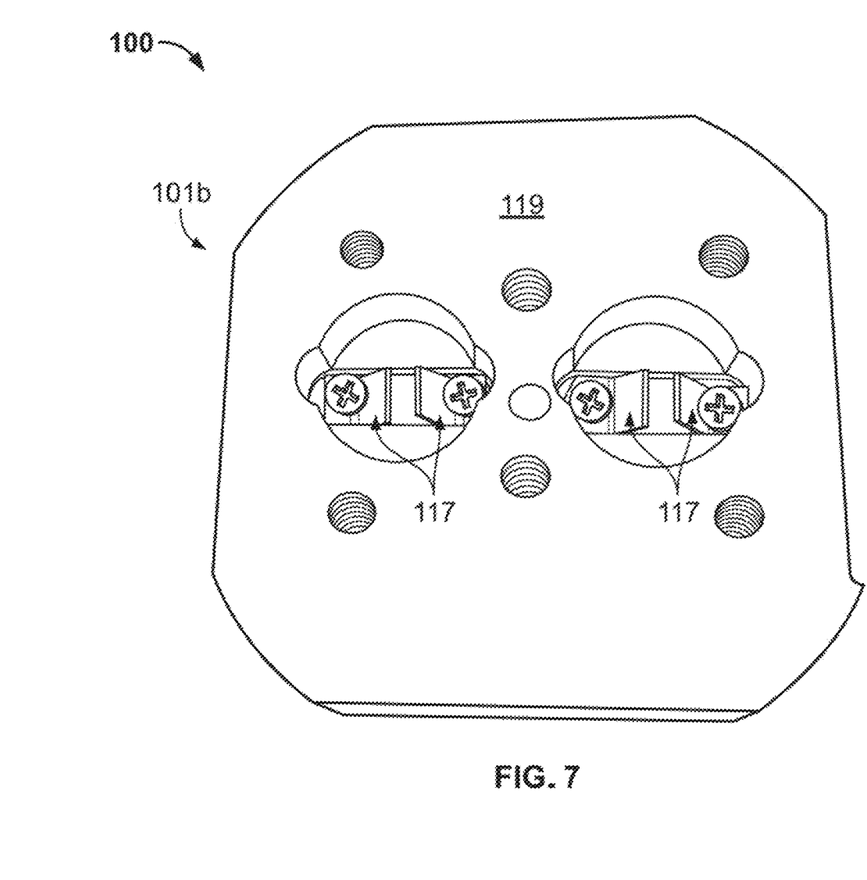

FIG. 7 is another view of the disassembled body 101 of the embodiment 100 showing the interior of the switch body 101b. When pressure is applied through the pressure body 101a the contacts 113 in the diaphragm are pushed into contact with the switch in the switch body 101b. The switch plates 117 are at different heights within the switch body 101b allowing the device 101 to sense two different pressures.

The switch body 101b houses the switch mechanism. It does not see pressure from the pneumatic otoscope but instead sees only atmospheric pressure. When pressure is applied through the pressure body 101a the contacts 113 in the diaphragm 114 are pushed into contact with the switch of the switch body 101b. The switch plates 117 are at different heights within the switch body 101b allowing the device 101 to sense two different pressures. The first switch can be calibrated to close the circuit at 200 dPa, the second at 400 dPa. Closing the circuit will apply electrical energy from the otoscope battery to LEDs letting the operator know when these pressures have been reached.

Unless defined otherwise, all technical and scientific terms used have the same meaning as commonly understood by one of ordinary skill in the art to which this disclosure belongs. Although any methods and materials similar or equivalent to those described can also be used in the practice or testing of the present disclosure, the preferred methods and materials are now described.

Embodiments of the present disclosure will employ, unless otherwise indicated, techniques of separating, testing, and constructing materials, which are within the skill of the art. Such techniques are explained fully in the literature.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

What is claimed is:

1. A calibrated pneumatic otoscope, comprising:
a power source;
a first light source operatively connected to the power source;
a housing operatively connected to the first light source;
an optical magnifying lens on an end of the housing;
a speculum on an end of the housing opposite the optical magnifying lens;
a light carrier to pass light from the first light source through an end of the speculum opposite the housing;
a pressure generating device in fluid connection with the housing; and
a safety valve operatively connected to a fluidic flow path of the pressure generating device; and
a pressure alert mechanism, wherein the pressure alert mechanism generates a first alert at a first effective pressure and a second alert at a second effective pressure, wherein the second effective pressure is higher than the first effective pressure.

2. The calibrated pneumatic otoscope of claim 1, wherein the fluidic flow path of the pressure generating device comprises a tube connecting the pressure generating device and the housing.

3. The calibrated pneumatic otoscope of claim 2, wherein the safety valve is operatively positioned in the fluidic flow path of the pressure generating device between the pressure generating device and the housing.

4. The calibrated pneumatic otoscope of claim 1, wherein the safety valve is operatively connected to the housing.

5. The calibrated pneumatic otoscope of claim 4, wherein the safety valve is positioned on the housing opposite the connection of a tube of the fluidic flow path with the housing.

6. The calibrated pneumatic otoscope of claim 1, wherein the safety valve is configured to release pressure from the otoscope at a pressure greater than about 300 daPa to about 400 daPa.

7. The calibrated pneumatic otoscope of claim 1, wherein the first effective pressure is greater than about 200 daPa to about 300 daPa.

8. A method of using a calibrated pneumatic otoscope of claim 1, comprising:
providing a calibrated pneumatic otoscope of claim 1; and
measuring the mobility of the tympanic membrane of a subject in need thereof with the calibrated pneumatic otoscope in response to pressure changes.

9. The method of claim 8, wherein the subject in need thereof has concerns for disease of the eardrum and middle ear.

10. A calibrated pneumatic otoscope, comprising,
a power source;
a first light source operatively connected to the power source;
a housing operatively connected to the first light source;
an optical magnifying lens on an end of the housing;
a speculum on an end of the housing opposite the optical magnifying lens;
a light carrier to pass light from the first light source through an end of the speculum opposite the housing;
a pressure generating device in fluid connection with the housing;
a safety valve; and
a pressure alert mechanism,
wherein the pressure alert mechanism generates a first alert at a lower effective pressure greater than about 200 daPa to about 300 daPa and a second alert at an upper effective pressure greater than about 300 daPa to about 400 daPa.

\* \* \* \* \*